United States Patent [19]

Harris et al.

[11] Patent Number: 5,663,455
[45] Date of Patent: Sep. 2, 1997

[54] PROCESS FOR CONDUCTING ETHERIFICATION REACTIONS USING AS CATALYSTS STRONG-ACID, CATION-EXCHANGE RESINS PREPARED UNDER HIGH TEMPERATURE CONDITIONS

[75] Inventors: William L. Harris, Midland, Mich.; Rex R. Stevens, Grand Junction, Colo.

[73] Assignee: The Dow Chemical Company, Midland, Mich.

[21] Appl. No.: 542,154

[22] Filed: Oct. 12, 1995

[51] Int. Cl.$^6$ .................................................. C07C 43/04
[52] U.S. Cl. ............................................................. 568/697
[58] Field of Search ................................................ 568/697

[56] References Cited

U.S. PATENT DOCUMENTS

| | | | |
|---|---|---|---|
| 2,922,822 | 1/1960 | Beach et al. | 260/614 |
| 3,037,052 | 5/1962 | Bortnick | 260/485 |
| 5,244,926 | 9/1993 | Harris et al. | 521/38 |

FOREIGN PATENT DOCUMENTS 1252153  11/1971  United Kingdom.

OTHER PUBLICATIONS

Konrad Dorfner (ed.), *Ion Exchangers*, Walter de Gruyter & Co., Berlin—New York 1991, pp. 1002–1009.

*Primary Examiner*—Marianne M. Cintins
*Assistant Examiner*—Dwayne C. Jones

[57] ABSTRACT

An improved process for conducting an etherification reaction has been discovered. The process employs a macroporous strong-acid, cation-exchange resin catalyst prepared at a temperature of about 120° C. or higher with a reduced amount of divinylbenzene crosslinker. The etherification catalysts produced in the invention display equivalent or superior catalytic activity than conventional catalysts and are less expensive to produce than conventional catalysts due to reduced amounts of crosslinker.

8 Claims, No Drawings

PROCESS FOR CONDUCTING ETHERIFICATION REACTIONS USING AS CATALYSTS STRONG-ACID, CATION-EXCHANGE RESINS PREPARED UNDER HIGH TEMPERATURE CONDITIONS

FIELD OF THE INVENTION

The present invention concerns an improved process for conducting etherification reactions in which a macroporous strong-acid, cation-exchange resin catalyst, which is prepared under high temperature conditions with a reduced amount of divinylbenzene crosslinker, is employed.

BACKGROUND OF THE INVENTION

Tertiary alkyl ethers, like methyl t-butyl ether (MTBE) and ethyl t-butyl ether (ETBE), are extremely useful as octane enhancers and fuel oxygenates in gasoline. These ethers are conveniently prepared by the acid-catalyzed electrophilic addition of primary alcohols to iso-butene. Commercially, certain strong-acid, cation-exchange resins prepared by sulfonating macroporous monovinyl aromatic monomer/divinylbenzene copolymers provide ideal physical and catalytic properties for such etherification reactions; see, for example, W. Neier in "Ion Exchangers," Konrad Dorfner, Ed., Walter de Gruyter, Berlin-New York, 1991, pp. 1002–1009. Strong-acid, cation-exchange resins specifically developed and sold for catalytic applications in t-alkyl ether manufacture, e.g., Rohm & Haas' Amberlyst™ A-15 and A-35 resins, Dow's Dowex™ M-3I resin and Purolite's CT-175 resin, are all derived from macroporous styrene/divinylbenzene copolymers having at least about 20 weight percent divinylbenzene crosslinker. Resins made from lower levels of crosslinker generally exhibit inferior catalytic activity.

U.S. Pat. No. 5,244,926 discloses the advantages of performing suspension polymerizations for producing monovinyl aromatic monomer/divinylbenzene copolymers under high temperature conditions attained adiabatically, i.e., under conditions in which a high temperature, about 120° C. or higher, of the reactor contents is reached by not removing the heat in the reactor that is generated by the polymerization reaction. These advantages include better reactor utilization, shorter reaction times and increased product throughput. The patent only teaches that these copolymers and resulting ion-exchange resins are useful to separate chemical species from solutions and to prepare polymeric adsorbents.

However, when suspension polymerizations using the recipes developed for commercial resins/copolymers are run at high temperatures, i.e. about 120° C. or higher reached adiabatically or otherwise, and the resins are subsequently sulfonated to prepare strong-acid, cation-exchange resins for use as etherification catalysts, the catalytic activity of the resulting resins is adversely affected, i.e., the rate of conversion of alcohol and olefin to ether is reduced. Another disadvantage associated with conventional processes is the high cost of the divinylbenzene crosslinker used therein. Thus, it would be very advantageous if a new process were available that could take full advantage of the benefits associated with a high temperature polymerization process without reducing the catalytic activity of the subsequently sulfonated monovinyl aromatic monomer/divinylbenzene copolymer products. In addition, it would be very commercially attractive if the new process to make the copolymer required less of a very expensive material, such as divinylbenzene crosslinker.

SUMMARY OF THE INVENTION

The present invention concerns an improved process for conducting etherification reactions in which a macroporous strong-acid, cation-exchange resin catalyst, which is prepared under high temperature conditions with a reduced amount of divinylbenzene crosslinker, is employed.

In prior processes, a monomer mixture of one or more monovinyl aromatic monomers and a divinylbenzene crosslinker, in an amount of at least about 20 weight percent, are polymerized in the presence of from about 25 to about 50 weight percent of an organic diluent, based on the total weight of monomers and diluent, in an aqueous suspension. The polymerization is carried out under high temperature conditions, i.e., the temperature of the reactor contents is about 120° C. or higher, to produce a macroporous copolymer which is subsequently sulfonated to produce a strong-acid, cation-exchange resin. The high temperature conditions, about 120° C. or higher, are reached either adiabatically and/or via an external means of adding heat. The improvement of the present invention comprises: decreasing the concentration of divinylbenzene crosslinker at least about 2, preferably at least about 4, weight percent to a range of from about 10 to about 18 weight percent of the monomer mixture, i.e., the monovinyl aromatic monomers and the divinylbenzene.

When the amounts of divinylbenzene used as a crosslinker in a high temperature, i.e., the temperature of the reactor contents is about 120° C. or higher, suspension polymerization of one or more monovinyl aromatic monomers are from about 10 to about 18 weight percent of monomer mixture, the resulting copolymers, after they are subsequently sulfonated to produce strong-acid, cation-exchange resins, are especially useful as catalysts for etherification reactions. Catalysts prepared with amounts outside this range at higher temperatures are generally less effective. Besides achieving the benefits associated with the high temperature process in preparing the resins, i.e., shorter reaction times and increased reactor capacity, the amounts and cost of the most expensive component, i.e. the divinylbenzene crosslinker, are reduced. Most surprisingly, the catalytic activity of said etherification catalysts prepared using from about 10 to about 18 weight percent of crosslinker equals or exceeds that of catalysts made employing conventional, at least about 20 weight percent, levels of crosslinker which are currently commercially used in etherification reactions.

DETAILED DESCRIPTION OF THE INVENTION

The copolymers of the present invention used to prepare the strong-acid, cation-exchange resins are typically in a macroporous bead matrix. The term "macroporous" is a well-known term of art describing the copolymer bead porosity and means that the copolymer has both mesopores and macropores. Mesopores have pore sizes of about 2 nanometers (nm) to about 50 nm while macropores have pore sizes of greater than about 50 nm to about 10,000 nm.

Strong-acid, cation-exchange resins are those cation-exchange resins having acid functional groups, such as sulfonic acid groups, substituted onto the copolymer bead matrix. The strong-acid, cation-exchange resins may then act as an acid catalyst in, for example, etherification reactions such as the production of primary $C_1$–$C_4$ alkyl t-butyl ethers from the reaction of a $C_1$–$C_4$ primary alcohol with iso-butene, e.g., methyl butyl ether produced from methanol and iso-butene and ethyl t-butyl ether produced from ethanol and iso-butene.

The macroporous copolymers used in this invention are typically prepared using suspension polymerization. Suspension polymerization comprises suspending droplets of a monomer or monomer mixture and an organic diluent (a solvent which typically dissolves the monomer or monomer mixture but not the copolymer) in a medium in which neither are soluble. This is usually accomplished by adding the monomer or monomer mixture and the organic diluent to a suspending medium, such as water, which contains a dispersing or suspending agent. When the medium is agitated, the organic phase (monomer and organic diluent) disperses into droplets. Polymerization is then accomplished by heating the suspension in the presence of a free radical initiator.

The suspension polymerization of the present invention is carried out under high temperature conditions. High temperature conditions means that the temperature of the reactor contents (typically a monomer mixture, organic diluent, suspending medium, dispersing or suspending agent, initiator, and any desired additives) reaches at least about 120° C., preferably at least about 130° C. during the suspension polymerization. Although any way of reaching these temperatures is useful, including addition of heat via external heating means in stages or continuously to the reactor contents throughout the polymerization, it is often most convenient that substantially adiabatic conditions are employed.

Substantially adiabatic conditions are conditions under which a substantial amount of the exothermic heat, usually about 40 percent or greater of the exothermic heat, preferably about 60 percent or greater of the exothermic heat, more preferably about 80 percent or greater of the exothermic heat, evolved during the suspension polymerization is retained within the suspension and results in a rise in the temperature of the reactor contents which is usually sufficient to sustain the polymerization reaction without further addition of heat. Typically, the retention of the exothermic heat evolved during the polymerization results in a rise in temperature of the reactor contents to at least about 120° C. preferably at least about 130° C. after polymerization has started.

The monovinyl aromatic monomer used in the present invention may be a mixture of one or more monomers as described, for example, in U.S. Pat. No. 5,244,926. Preferably, the monovinyl aromatic monomer or monomers include styrene or ethyl vinylbenzene or mixtures thereof. As known in the art, other monomers, such as acrylates and acrylonitriles, may be present in the monomer mixture in order to control and effect the properties of the resulting copolymer beads, e.g., bead porosity or bead strength.

The divinylbenzene crosslinker is employed in a concentration of from about 10 to about 18, preferably from about 12 to about 18, more preferably from about 14 to about 16, weight percent of the monomer mixture of monovinyl aromatic monomers and polyvinyl aromatic crosslinking monomers. This amount has been found to maximize the catalytic activity of the cationic resins derived from the copolymer produced during the high temperature suspension polymerization. Maximized catalytic activity of the etherification catalyst results in a maximized rate of conversion in the production of ethers from alcohols and olefins. The increased rate can increase the amount of methyl t-butyl ether produced from the reaction of methanol and iso-butene or the amount of ethyl t-butyl ether produced from the reaction of ethanol and iso-butene when the cationic resin catalysts are produced from copolymers produced at high temperatures and having a concentration of from about 10 to about 18, preferably from about 12 to about 18, more preferably from about 14 to about 16, weight percent divinylbenzene as the crosslinker. This concentration of divinylbenzene as crosslinker not only results in increased catalytic activity, but it also significantly reduces the cost of copolymer production as divinylbenzene is typically the more expensive of the raw materials.

The organic diluents/solvents useful in the present invention are those solvents which are suitable for forming pores and/or displacing the insoluble polymer chains during polymerization. The characteristics and use of such diluents/solvents in the formation of macroporous resins are described in U.S. Pat. No. 4,224,415. These diluents/solvents may be any of the ones, or mixtures of the ones, which are described in, for example, U.S. Pat. Nos. 4,224,415 or 5,231,115. Typically, $C_6$–$C_{12}$ saturated aliphatic hydrocarbons, such as heptane and iso-octane, and the $C_4$–$C_{10}$ alkanols, such as t-amyl alcohol, sec-butanol and 2-ethylhexanol, are particularly effective. A sufficient concentration of the organic diluent is required to effect phase separation or polymer chain displacement. Typically, the organic diluent comprises from about 25 to about 50 weight percent of the total weight of the monomer mixture and diluent.

The free radical initiator or combination of such initiators may be any compound or compounds capable of generating free radicals in the polymerization of vinyl aromatic monomers. Suitable initiators are mentioned in, for example, U.S. Pat. Nos. 4,192,921; 4,246,386; and 4,283,499. Azo-compounds like azobisisobutyronitrile and peroxygen compounds such as benzoyl peroxide, t-butylperoctoate, and t-butylperbenzoate may usually be employed with most vinyl aromatic monomers. The amount of initiator or combination of initiators used will vary with the type of initiator and type and proportion of monomers being polymerized as those skilled in the art will appreciate. Generally, from about 0.02 to about 1 weight percent of the initiator based on total weight of monomer mixture is adequate.

The suspending medium used in the process of the present invention is usually water containing a suspending agent such as gelatin, polyvinyl alcohol or a cellulosic such as hydroxyethyl cellulose, methyl cellulose or carboxymethyl methyl cellulose. Generally, the suspending medium is employed in an amount of at least about 35 volume percent of the total volume of the organic phase (monomer mixture and porogenic solvent) and suspending medium. However, the amount of the suspending medium employed should not be below the point where suspension failure occurs. That is, the continuous phase of the suspending medium/monomer mixture must be the suspending medium, typically water, and the suspended monomer mixture must remain dispersed in the medium. Usually, the lower limit for the amount of suspending medium is about 35 volume percent of the total volume of the organic phase (monomer mixture and porogenic solvent) and suspending medium.

Polymerization usually begins when the temperature of the suspending medium is raised to at least about 40° C. preferably to at least about 70° C. and no more than about 120° C. by applying initial heat from an external source. If staged suspension polymerization, i.e., not substantially adiabatic, is employed, more heat is added or excess heat is removed externally in stages or continuously until the temperature of the reactor contents reaches at least about 120° C. and preferably to at least about 130° C. and remains at that temperature until at least about 70 weight percent, preferably at least about 80 weight percent, most preferably until at least about 90 weight percent of the polymerizable monomer based on total weight of monomer has polymerized.

Most preferably, substantially adiabatic conditions are employed for reasons stated above. In this case, the temperature of the suspending medium is raised to at least about 40° C., preferably to at least about 70° C. and no more than about 120° C. by applying heat from an external source. The heat is added or the raised temperature is maintained until at least the time when the exothermic heat evolved from polymerization of the monomers to copolymer is sufficient to maintain the polymerization without further addition of heat to the suspending medium. Utilizing substantially adiabatic conditions, the temperature of the reactor contents will advantageously increase to at least about 120° C., and preferably to at least about 130° C., for a time sufficient to polymerize at least about 80 weight percent, preferably at least 90, more preferably at least about 99 weight percent, or more of the polymerizable monomers.

The copolymers may be functionalized to strong-acid, cation-exchange resin catalysts by any method capable of adding sulfonic acid groups onto the copolymer bead matrix, for example, as shown in U.S. Pat. Nos. 3,266,007; 2,500,149; 2,631,127; 2,664,801; and 2,764,564. Typically, functionalization using sulfuric acid and chlorinated solvent as a swelling solvent is effective. However, if a higher degree of sulfonation is desired, i.e., more than one sulfonate group per aromatic nucleus, then a variety of supersulfonating agents may be employed as will be apparent to one skilled in the art. For example, oleum, i.e., fuming sulfuric acid, may be employed as discussed in U.S. Pat. No. 4,839,331. Once functionalized, the strong-acid, cation-exchange resins are useful in catalyzing etherification reactions and particularly useful in the production of methyl t-butyl ether from methanol and iso-butene or in the production of ethyl t-butyl ether from ethanol and iso-butene.

The invention is further illustrated by the following examples.

EXAMPLE 1

A 12/32 (12 percent divinylbenzene by weight of the total monomers/32 percent diluent by weight of the total organic phase) strong acid macroporous cation exchange resin catalyst was prepared in the following manner.

Batch polymerizations were conducted in a 2-liter (L) stainless steel reactor equipped with agitation. The monomer phase comprised 338 grams (g) styrene, 52 g of active divinylbenzene in solution (55 percent divinylbenzene, 44 percent ethyl vinylbenzene, and 1 percent diethyl benzene), 2.31 g of 50 percent tert-butyl peroctoate and 0.77 g tert-butyl perbenzoate. Thus, the total monomers weighed 433 g and were mixed with 203 g of commercial isooctane. The aqueous phase comprised 504 g water, 130 g of 1 percent carboxy methyl methyl cellulose (suspending agent) and 2.4 g of 60 percent sodium dichromate (latex polymerization inhibitor). Both phases were loaded into the reactor, which was then sealed and pressure tested. The reactor was purged with nitrogen and the agitation revolutions per minute (rpm) was set. The reactor temperature was ramped to 80° C. to initiate the monomer charge and heated as fast as possible, i.e., in about one-half hour, to the final adiabatic temperature (170° C.) to simulate the self-heat ramp which would occur if the reaction were run on a larger scale. The reactor was held at that temperature for one hour and then cooled. The copolymer was recovered from the reactor, washed, steam-stripped, filtered, dried, and sieved. The copolymer in the form of beads was functionalized by sulfonating with an excess of 99 percent sulfuric acid in the absence of a swelling solvent. The sulfonated beads were hydrated with increasingly diluted sulfuric acid and then backwashed with deionized water to form a strong acid macroporous cation exchange resin catalyst.

EXAMPLE 2

A 14/32 (14 percent divinylbenzene by weight of the total monomers/32 percent diluent by weight of the total organic phase) strong acid macroporous cation exchange resin catalyst was prepared in the same manner as Example 1 except that 61 g of active divinylbenzene in solution (55 percent divinylbenzene, 44 percent ethyl vinylbenzene, and 1 percent diethyl benzene) and 322 g of styrene were employed.

EXAMPLE 3

A 16/30 (16 percent divinylbenzene by weight of the total monomers/30 percent diluent by weight of the total organic phase) strong acid macroporous cation exchange resin catalyst was prepared in the same manner as Example 1 except that 69 g of active divinylbenzene in solution (55 percent divinylbenzene, 44 percent ethyl vinylbenzene, and 1 percent diethyl benzene) and 308 g of styrene were employed and the final adiabatic temperature was 165° C.

EXAMPLE 4

A 18/32 (18 percent divinylbenzene by weight of the total monomers/32 percent diluent by weight of the total organic phase) strong acid macroporous cation exchange resin catalyst was prepared in the same manner as Example 1 except that 78 g of active divinylbenzene in solution (55 percent divinylbenzene, 44 percent ethyl vinylbenzene, and 1 percent diethyl benzene) and 291 g of styrene were employed.

The strong acid macroporous cation exchange resin catalysts prepared in Examples 1, 2, 3, and 4 were ground, sieved, and tested for catalytic activity in methyl tert-butyl ether production by the following method. The tested resin catalysts of Examples 1–4 displayed equivalent, within experimental error, or superior yields compared to strong acid macroporous cation exchange resin catalysts produced at high temperatures having conventional, i.e., about 20 percent divinylbenzene by weight of the total monomers, amounts of divinylbenzene crosslinker. The results are summarized in Table I.

The laboratory system used to test cation resin catalysts consisted of a stainless steel reaction mixture feed tank, a Beckman 110B high pressure liquid chromotography (HPLC) pump, a 1.6 centimeter by 20.3 centimeter stainless steel reactor contained in a heated aluminum block, and a pressure control valve all connected with 0.16 centimeter stainless steel tubing and needle valves. The reactor was capped on both ends and fitted with a thermocouple well and a 10 cubic centimeter (cc) bed of glass beads contained between two plugs of glass wool. A 12 cc bed of catalyst could be loaded into the reactor on top of the glass bead bed. The reactor was contained in a 5.1 centimeter diameter by 20.3 centimeter long aluminum block fitted with a thermocouple and two 100 watt electric heaters connected to a temperature controller. A premixed reaction mixture containing 11 percent methanol, 17 percent iso-butene, and 72 percent butane was pumped to the reactor from a 1 liter, stainless steel feed tank by a Beckman 110B HPLC pump. The 1 liter feed tank could be periodically filled from a larger cylinder (35 liter) of the reaction mixture. Pressure in the reactor was controlled by a control valve pneumatically activated by a pressure transducer and a pressure controller. The system was piped through two pneumatically activated rotary valves to allow analysis of both the feed mixture and the product mixture. To avoid explosion hazards, the system was set up in a dedicated hood containing no other electrical equipment and the HPLC pump was continuously purged with nitrogen.

Analysis of the reaction mixture or the product mixture was conducted by gas chromatography using a Hewlett Packard 5890 gas chromatograph fitted with a CHROMPAK™ 10M PORAPLOT™ U column, a flame ionization detector, and an automated sampling and sample injection system which allowed an analysis of the feed mixture or product mixture every 20 minutes. Detector response factors for each of the components to be analyzed (MeOH, isobutene, butane and MTBE) were obtained using a mixture containing weighted amounts of each component.

In a typical catalyst evaluation, water was removed from a 20 cc portion of cation resin by chromatographic washing with approximately 200 milliliters (ml) of dry methanol in a column. A vibrator packed, 12 cc portion of the methanol wet resin was loaded into the reactor and a glass wool plug was placed on top of the resin bed to prevent resin loss during a run. In some runs, the resin was broken in a blender and screened to give minus 60 to plus 70 mesh (210 to 250 micron) resin which was then washed with dry methanol and loaded in the reactor. After the reactor was placed in the heated aluminum block and re-attached to the system, thermocouples were placed in a hole in the aluminum block and in the thermocouple well of the reactor. The HPLC pump was turned on at a flow rate of 0.6 to 1.2 milliliters per minute (ml/min) and the system was pumped up to 2.38 MPa (200 pounds per square inch gauge) pressure. The heaters were then turned on and the aluminum block was heated to a desired temperature (usually between 45° and 55° C.). The maximum temperature in the catalyst bed was monitored by correctly positioning the thermocouple in the thermocouple well of the reactor at each chosen flow rate. Depending on the reaction mixture flow rate, the reaction exotherm usually gave a 3° to 7° C. higher temperature in the catalyst bed than in the heated block. Catalyst evaluations were conducted at two different flow rates, 3 bed volumes per hour (BV/hr) at 50° C. maximum temperature in the catalyst bed and 6 BV/hr at 60° C. maximum temperature in the catalyst bed. After reaching the desired temperature at a given flow rate, the reactor was allowed to run until equilibrium conditions were established and the concentration of MTBE in the product mixture remained relatively constant for at least three consecutive sample analyses. The yield of MTBE was calculated from the average concentration in the last three samples divided by the calculated concentration at 100 percent MTBE yield based on isobutene in the feed mixture. Results of the MTBE yield for ground and sieved particles of 210-250 microns in size for Examples 1, 2, 3, and 4 are summarized in Table 1 below.

TABLE 1

| Catalyst | MTBE percent yield (%) | |
|---|---|---|
| | 50° C. 3 BV/Hr | 60° C. 6 BV/Hr |
| Example 1 12% DVB (210–250 microns) | 81 | 85 |
| Example 2 14% DVB (210–250 microns) | 86 | 87 |
| Example 3 16% DVB (210–250 microns) | 89 | 92 |
| Example 4 18% DVB (210–250 microns) | 86 | 89 |

What is claimed is:

1. In a method for conducting an etherification reaction employing as the catalyst a strong-acid, cation-exchange resin, wherein said resin is prepared by a process in which a monomer mixture comprising one or more monovinyl aromatic monomers and a divinylbenzene crosslinker in an amount of at least about 20 weight percent are polymerized in the presence of from about 25 to about 50 weight percent of an organic diluent, based on the total weight of monomers and diluent, in an aqueous suspension the reactor contents of which attain a temperature above about 120° C. during the polymerization producing a macroporous copolymer which is subsequently sulfonated to produce the strong-acid, cation-exchange resin, the improvement in preparing the copolymer which comprises: decreasing the concentration of divinylbenzene crosslinker at least about 2 weight percent to a range of from about 14 to about 18 weight percent of the monomer mixture.

2. The method of claim 1 wherein the concentration of divinylbenzene crosslinker is from about 14 to about 16 weight percent of the monomer mixture.

3. The method of claim 2 in which the $C_1$ to $C_4$ primary alkanol is methanol.

4. The method of claim 2 in which the $C_1$ to $C_4$ primary alkanol is ethanol.

5. The method of claim 1 wherein the monomer mixture comprises styrene or ethyl vinylbenzene or mixtures thereof.

6. The method of claim 1 wherein the etherification reaction comprises reacting a $C_1$ to $C_4$ primary alkanol with iso-butene.

7. The method of claim 1 in which the temperature of the reactor contents has been attained under conditions wherein heat is added via an external means.

8. The method of claim 1 in which the temperature of the reactor contents has been attained under substantially adiabatic conditions.

* * * * *